(12) United States Patent
Wang et al.

(10) Patent No.: US 10,217,252 B1
(45) Date of Patent: Feb. 26, 2019

(54) SEE-THROUGH SENSING FOR IMAGE RECONSTRUCTION OF STRUCTURE OF TARGET OBJECT

(71) Applicant: Mitsubishi Electric Research Laboratories, Inc., Cambridge, MA (US)

(72) Inventors: Pu Wang, Cambridge, MA (US); Toshiaki Koike Akino, Lexington, MA (US); Haoyu Fu, Cambridge, MA (US); Philip Orlik, Cambridge, MA (US)

(73) Assignee: Mistubishi Electric Research Laboratories, Inc., Cambridge, MA (US)

( * ) Notice: Subject to any disclaimer, the term of this patent is extended or adjusted under 35 U.S.C. 154(b) by 0 days.

(21) Appl. No.: 16/027,671

(22) Filed: Jul. 5, 2018

(51) Int. Cl.
*G01N 21/55* (2014.01)
*G01N 21/88* (2006.01)
*G06T 11/00* (2006.01)

(52) U.S. Cl.
CPC ............ *G06T 11/008* (2013.01); *G01N 21/55* (2013.01); *G01N 21/8851* (2013.01); *G01N 2021/8887* (2013.01)

(58) Field of Classification Search
CPC ............... G01N 21/55; G01N 21/8851; G01N 2021/8887; G06T 11/008
See application file for complete search history.

(56) References Cited

U.S. PATENT DOCUMENTS

2010/0007872 A1\* 1/2010 Isozaki .................. G01N 21/47 356/51
2013/0176309 A1\* 7/2013 Sarkis .................... G01V 8/005 345/422

\* cited by examiner

*Primary Examiner* — Mark R Gaworecki
(74) *Attorney, Agent, or Firm* — Gene Vinokur; James McAleenan; Hironori Tsukamoto

(57) ABSTRACT

A scanner includes an emitter configured to emit a wave in a direction of propagation to penetrate layers of a structure of a target object and a receiver configured to measure intensities of the wave reflected by the layers of the target object. The scanner also includes a hardware processor configured to partition the intensities of the reflected wave into a set of segments, such that each segment is the reflection from a corresponding layer of the target object, defining a multi-layered structure of the target object; and reconstruct images of the layers of the target object from corresponding segments using a joint-layer hierarchical image recovery that prevents an increase in sparsity of the layers of the target object in the direction of propagation of the wave. An output interface is configured to render the reconstructed images of layers of the target object.

20 Claims, 17 Drawing Sheets

*(Raster Scanning with single THz transceiver for Multi-Layer Non-Overlapping Code Patterns)*

(Raster Scanning with an array of THz transceivers for Multi-Layer Non-Overlapping Code Patterns)

(Compressed Scanning with single THz transceiver for Multi-Layer Non-Overlapping Code Patterns)

*(Transmission Mode: Compressed Scanning with single THz transceiver for Multi-Layer Non-Overlapping Code Patterns)*

SEE-THROUGH SENSING FOR IMAGE RECONSTRUCTION OF STRUCTURE OF TARGET OBJECT

TECHNICAL FIELD

This invention relates to see-through sensing, and more specifically to system and method for image reconstruction of structure of target object.

BACKGROUND

See-through sensing is important for many applications such as microwave imaging, biomicroscopy, medical imaging, through-the-wall imaging (TWI), infrastructure monitoring, and seismic imaging. In particular, the see-through sensing enables the visualization of the internal structure of the material and characterization of its physical properties. For example, in microwave imaging, the see-through sensing provides the structure of objects. In biomicroscopy, the see-through sensing allows to visualize the internal cell structure in three-dimensions. In TWI, the see-through sensing allows to compensate for the delay of the signal propagating through the wall.

For example, over the past two decades, there have been increased interests in terahertz (THz) sensing, in either a reflection or a transmission mode, due to the broad applications in gas sensing, moisture analysis, non-destructive evaluation, biomedical diagnosis, package inspection, and security screening. The THz sensing systems are able to inspect not only the top surface of the sample but also its internal structure, either a defect underneath the top layer or a multi-layer structure, due to its capability of penetrating a wide range of non-conducting materials.

However, the see-through sensing, such as THz sensing, suffers from complexity in image reconstruction of three-dimensional objects. In addition, to the complexity of computation, undesirable artifacts can diminish the quality of reconstructed images. Accordingly, there is a need for a system and a method for image reconstruction of a structure of a target object.

SUMMARY

It is an object of some embodiments to provide a system and a method for image reconstruction of a structure of a target object. Some embodiments are based on recognition that in a number of situations, the structure of the target object is sparse, and the sparsity can be used in the image reconstruction. However, the image reconstruction of sparse but three-dimensional structures is still a computationally challenging problem.

Some embodiments are based on realization that this problem can be addressed by treating the structure of the target object as a multi-layer structure and reconstructing the images of each layer of the target object individually and/or jointly. Such a multi-layer representation of the structure allows to consider not only the sparsity of the entire structure of the target object, but also the sparsity of each individual layer. In addition, such a multi-layer representation allows partitioning and, thus, simplifying the computation of the image reconstruction.

For example, some embodiments partition the intensities of the reflected wave into a set of segments. This segmentation is typically happening in response to emitting a wave in a direction of propagation to penetrate layers of a structure of a target object and measuring intensities of the wave reflected by the layers of the target object. Such a segmentation defines the multi-layer structure of the target object, i.e., each segment is the reflection from a corresponding layer of the target object. To that end, some embodiments reconstruct images of the layers of the target object from corresponding segments, as contrasted with reconstructing one image of the entire object from the entire reflected wave.

It should be noted that, in a number of situations, the structure of the target object is indeed layered. For example, a target object can be a man-made object with a layered structure, such as a stack of papers, where each sheet of paper is a layer in that multi-layer structure, a semiconductor device formed by layers of different materials, and infrastructure extended underground at different depths. For example, a target object can be a natural object with a layered structure, such as human tissue having multiple layers. In those situations, the layers of the multi-layered structure can be identified by peak finding method searching for peaks of the intensities of the wave reflected by the layers of the target object.

In other situations, however, the target objects do not have a clearly observed layered structure, and the segmentation is performed using different techniques, such as time gating with uniform or non-uniform gate periods. In any case, in some embodiments, the target object is considered as a multi-layered structure with layered defined by the segmentation of the reflected wave.

Some embodiments are based on recognition that the images of the layers of the target object can be reconstructed individually and/or jointly. Some embodiments reconstruct the images using sparse reconstruction by fitting reconstructed images into the measurements of the intensities of the reflected wave. Such a sparse reconstruction is performed with regularization to prevent overfitting. Different embodiments perform the individual and/or joint reconstruction of the layers by selecting an appropriate regularization. For example, for individual reconstruction, the regularizations are individual for each layer. In contrast, for a joint reconstruction, the regularization is a joint regularization determined as a weighted combination of individual regularizations of the layers.

However, after a number of experiments, simulations, and testing, some embodiments identify additional problems of layered reconstruction. Indeed, why computational performance has been improved, the image quality of reconstructed images of the layers suffered. This quality degradation is more noticeable on the images of the deeper layers. This problem is partially addressed by the joint reconstruction, but still, in a number of experiments, the images of the deeper layers reconstructed using individual and/or joint reconstruction include artifacts.

Some embodiments are based on recognition that despite the advantages of treating a target object as a layered-structure, such a treatment creates an additional problem in the multi-level image reconstruction. Specifically, the multi-level image reconstruction suffers from shadow effect due to the non-uniform penetrating of the wave from front layer to deeper layers. This problem can be conceptualized as a structure of one layer casts a shadow on subsequent layers and that shadow can be considered as the structure of the subsequent layers. In such a manner, the shadow effect contributes to the artifacts in the image reconstruction of the deep layers.

Some embodiments are based on realization that the shadow effect prevents an increase in sparsity of the layers of the target object in the direction of propagation of the wave penetrating the layers of the object. Indeed, if each subsequent layer has a shadow effect from a previous layer, the subsequent layer is at least as sparse as the previous layer, but usually is less sparse. To that end, some embodiments are based on realization that if such a constraint is enforced on joint images reconstruction of the layers, such a constraint forces the reconstruction to consider shadow effect to reduce the unwanted artifacts.

To that end, some embodiments disclose a joint-layer hierarchical image recovery that prevents an increase in sparsity of the layers of the target object in the direction of propagation of the wave. For example, the increase in sparsity of the layers can be prevented by imposing hierarchical joint sparsity constraints on image reconstruction.

For example, some embodiments, instead of using individual or joint regularization on image reconstruction, use a joint hierarchical regularization. The joint hierarchical regularization is a weighted combination of joint regularizations of group of layers, each group of layers includes a layer selected from the multi-layered structure as well as all layers preceding the layer in the multi-layer structure. In this context, a joint regularization of a group of layers is a weighted combination of individual regularizations of the layers in the group.

For example, in one embodiment the joint-layer hierarchical image recovery uses a joint-layer hierarchical regularized least square method minimizing a combination of a first term and a second term. The first term imposes a joint data fitting across all reconstructed images of all layers of the multi-layer structure to the measured intensities of the reflected wave, while the second term imposes the joint hierarchical regularization on recovered content of the reconstructed images of the multi-layer structure. In such a manner, the joint-layer hierarchical image recovery can take advantage from joint image reconstruction while considering the shadow effect.

The joint hierarchical regularization promotes a nested group sparsity to consider shadow effect on the deeper layers. In some embodiments, nested group sparsity is enforced in total variation (TV) domain, which is advantageous for image reconstruction. For example, in some embodiments, the joint hierarchical regularization includes a TV of amplitudes of the measured intensities of the reflected wave. Examples of TV include one or combination of an isotropic TV and anisotropic TV. This allows the joint-layer hierarchical image recovery to minimize TV of amplitudes of the measured intensities of the reflected wave subject to hierarchical joint sparsity constraints.

Different embodiments use different types of emitters selected based on an expected structure of the target object and desired type of image reconstruction. Examples of emitters include optical, ultrasound, and x-ray emitters. Some embodiments use terahertz (THz) emitters emitting within a terahertz frequency range, e.g., from 0.3 to 3 terahertz with corresponding wavelengths from 1 mm to 0.1 mm (or 100 μm). Because THz scanners are sensitive to non-uniform penetrating illumination from front layers to deep layers, the joint-layer hierarchical image recovery benefits these kinds of emitters.

Additionally, or alternatively, some embodiments use scanners that operate in a compressed scanning mode. This type of scanner can further decrease the dependency on non-uniform penetration due to principles of compressed reconstruction. For example, in one embodiment, the emitter includes a collimator to collimate the wave to a broad beam, and a spatial encoder to spatially encode the broad beam with a random mask. In addition, the receiver includes a focusing lens to focus the reflected wave, and a single-pixel photoconductive detector receiving the focused wave from the focusing lens to provide one measurement of the focused wave at a time allowing to recover the image of the multi-layer structure using a sparse reconstruction.

Some embodiments are based on another realization that the performance of joint-layer hierarchical image recovery can be improved when structural patterns of different layers of the target object are not overlapping in the direction of propagation of the wave. In such a manner, the shadow effect does not interfere with the structure of the subsequent layers. Some embodiments are based on recognition that in a number of situation, the structure of the target object is sparse enough to assume the non-overlapping patterns of different layers. Additionally, or alternatively, some embodiments design the target object in such a way as to ensure the not-overlapping patterns.

For example, in one embodiment the target object is a shipping label having an address printed on a first layer, and having a name of addressing printed on a second layer. The name and the address printed on different layers of the shipping label are not overlapping, and the name printed at the subsequent layer allows to preserve the confidentiality of the addressee. In another embodiment, the target object is an identification card having different identification codes printed on different layers of the identification card. Such an identification card allows to address a counterfeiting problem. In another embodiment, the target object is a position encoding structure having different codes printed on different layers of the position encoding structure. This embodiment allows to print a more dense code on multiple layers than a code printed only at a single layer.

Accordingly, one embodiment discloses a scanner that includes an emitter configured to emit a wave in a direction of propagation to penetrate layers of a structure of a target object; a receiver configured to measure intensities of the wave reflected by the layers of the target object; a hardware processor configured to partition the intensities of the reflected wave into a set of segments, such that each segment is the reflection from a corresponding layer of the target object, defining a multi-layered structure of the target object; and reconstruct images of the layers of the target object from corresponding segments using a joint-layer hierarchical image recovery that prevents an increase in sparsity of the layers of the target object in the direction of propagation of the wave; and an output interface to render the reconstructed images of layers of the target object.

Another embodiment discloses a method for image reconstruction of a structure of a target object, wherein the method uses a processor coupled with stored instructions implementing the method, wherein the instructions, when executed by the processor carry out steps of the method that includes accepting intensities of the reflected wave, in response to emitting a wave in a direction of propagation to penetrate layers of a structure of a target object and measuring the intensities of the wave reflected by the layers of the target object; partitioning the intensities of the reflected wave into a set of segments, such that each segment is the reflection from a corresponding layer of the target object, defining a multi-layered structure of the target object; reconstructing images of the layers of the target object from corresponding segments using a joint-layer hierarchical image recovery that prevents an increase in sparsity of the layers of the target object in the direction of propagation of the wave; and rendering the reconstructed images of layers of the target object.

Yet another embodiment includes a non-transitory computer readable storage medium embodied thereon a program executable by a processor for performing a method, the method includes accepting intensities of the reflected wave, in response to emitting a wave in a direction of propagation to penetrate layers of a structure of a target object and measuring the intensities of the wave reflected by the layers of the target object; partitioning the intensities of the reflected wave into a set of segments, such that each segment is the reflection from a corresponding layer of the target object, defining a multi-layered structure of the target object; reconstructing images of the layers of the target object from corresponding segments using a joint-layer hierarchical image recovery that prevents an increase in sparsity of the layers of the target object in the direction of propagation of the wave; and rendering the reconstructed images of layers of the target object.

DETAILED DESCRIPTION

Figure 1:
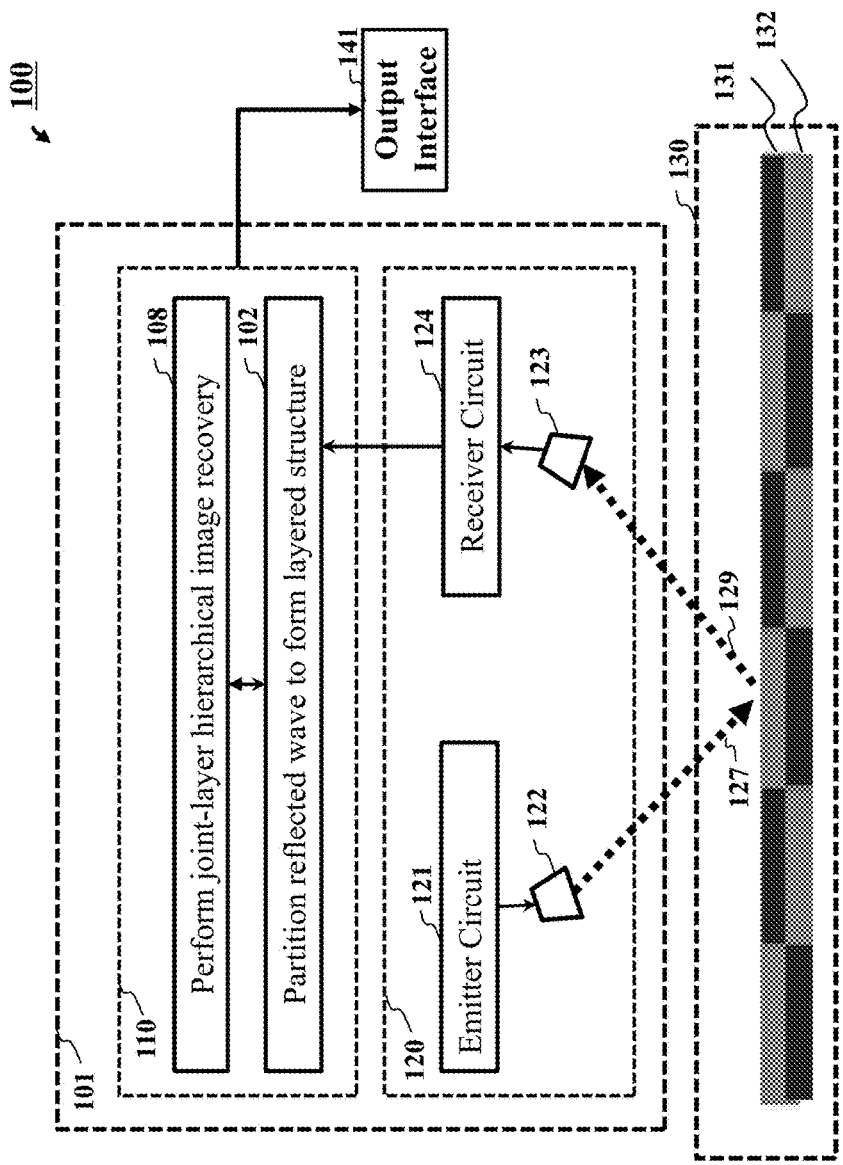
FIG. 1 shows a schematic of a scanner according to some embodiments.

FIG. 1 shows a schematic of a scanner 100 according to some embodiments. The scanner includes a sensing system 120 that includes an emitter 121 and a receiver 124. The emitter is configured to emit a wave 127 from an antenna 122 in a direction of propagation to penetrate layers 131-132 of a structure of a target object 130. The receiver 124 is configured to measure intensities of the wave reflected 129 by the layers of the target object 130 and accepted through an antenna 123.

The scanner 100 includes a computer-based information system 110 including a hardware processor configured to partition 102 the intensities of the reflected wave into a set of segments, such that each segment is the reflection from a corresponding layer of the target object, defining a multi-layered structure of the target object. The processor reconstructs 108 images of the layers of the target object from corresponding segments using a joint-layer hierarchical image recovery that prevents an increase in sparsity of the layers of the target object in the direction of propagation of the wave. The scanner 100 also includes an output interface 141 to render the reconstructed images of layers of the target object.

The scanner 100 treats the structure of the target object 130 as a multi-layer structure that allows to consider not only the sparsity of the entire structure of the target object, but also the sparsity of each individual layer. In addition, such a multi-layer representation allows partitioning and, thus, simplifying the computation of the image reconstruction.

For example, some embodiments partition the intensities of the reflected wave into a set of segments. This segmentation is typically happening in response to emitting a wave in a direction of propagation to penetrate layers of a structure of a target object and measuring intensities of the wave reflected by the layers of the target object. Such a segmentation defines the multi-layer structure of the target object, i.e., each segment is the reflection from a corresponding layer of the target object. To that end, some embodiments reconstruct images of the layers of the target object from corresponding segments, as contrasted with reconstructing one image of the entire object from the entire reflected wave.

It should be noted, that in a number of situations, the structure of the target object is indeed layered. For example, a target object can be a man-made object with a layered structure, such as a stack of papers, where each sheet of paper is a layer in that multi-layer structure, a semiconductor device formed by layers of different materials, and infra-structure extended underground at different depths. For example, a target object can be a natural object with a layered structure, such as human tissue having multiple layers. In those situations, the layers of the multi-layered structure can be identified by pick finding method searching for picks of the inequities of the wave reflected by the layers of the target object.

In other situations, however, the target objects do not have a clearly observed layered structure, and the segmentation can be performed using different techniques, such as time gating with uniform and/or non-uniform gate periods. In any case, in some embodiments, the target object is considered as a multi-layered structure with layered defined by the segmentation of the reflected wave.

For example, let $x_l = [x_l(1), x_l(2), \ldots, x_l(N)]^T$ denote a reflectance vector by stacking the columns of the two-dimensional reflectance matrix at the l-th layer of the sample, where N is the number of total pixels at each layer of the sample. For example, let an emitter, such as the THz source, illuminate the target object from a spatially encoded mask. Then, the received measurements can be described as $$y_l = A_l x_l + v_l, \quad (1)$$

where $A_l = [a_{l,1}, \ldots, a_{l,M}]^T$ is the measurement matrix corresponding to the l-th layer, $v_l = [v_l(1), \ldots, v_l(M)]^T$ is the Gaussian distributed noise with zero mean and an unknown variance $\sigma_l^2$, i.e., $v_l$: $N(0, \sigma_l^2 I_M)$, $y_l = [y_l(1), \ldots, y_l(M)]^T$, and M is the number of measurements.

In practice, the THz-band SLM likely remains the same during the electro-optic sampling process which leads to the same measurement matrix A over all layers. Some embodiments, however, assume the measurement matrix $A_l$ is a function of the layer index as the measurement matrix can absorb layer-dependent inter-reflections and surface irregularity.

It is noticed that the signal model of (1) can, in fact, describe both raster and compressed scanning acquisitions. For example, in the case of the raster scanning, i.e., each pixel is illuminated and measured individually, M=N and A reduces to a diagonal matrix with diagonal elements responsible for the depth variation. In the case of the compressed scanning, e.g., the single-pixel THz camera, M<N and each row of the measurement matrix A corresponds to one random mask pattern used to form one measurement $y_m$. In the case of layered structures, the shadow effect is present due to the non-uniform penetrating illumination from front layers to deeper layers.

Figure 2:
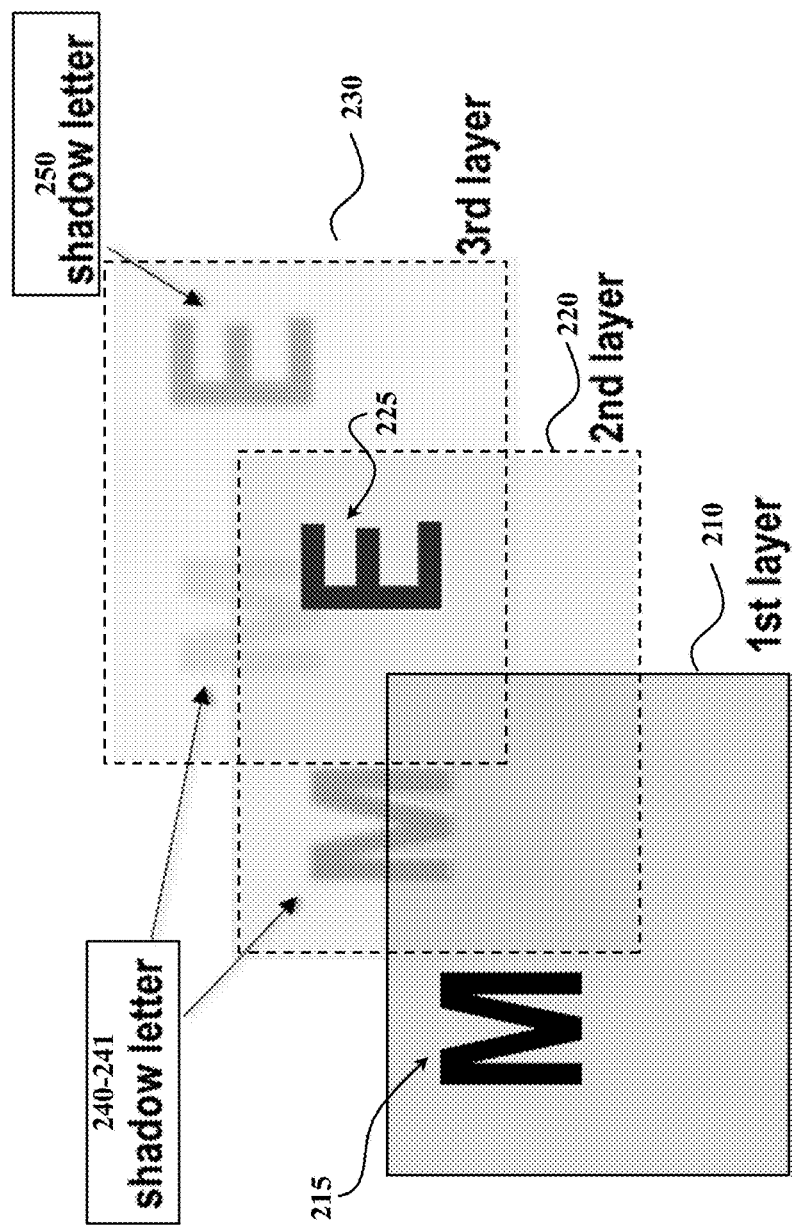
FIG. 2 shows a schematic of an exemplar target structure according to one embodiment.

FIG. 2 shows a schematic of an exemplar target structure according to one embodiment. In this example, the target structure man-made object with a layered structure, i.e., a stack of three sheet of papers. This example illustrate a problem of image reconstruction created by treating the target object as a layered structure.

Specifically, some embodiments are based on recognition that the images of the layers of the target object can be reconstructed individually and/or jointly. Some embodiments reconstruct the images using sparse reconstruction by fitting reconstructed images into the measurements of the intensities of the reflected wave. Such a sparse reconstruction is performed with regularization to prevent overfitting. Different embodiments perform the individual and/or joint reconstruction of the layers by selecting an appropriate regularization. For example, for individual reconstruction, the regularizations are individual for each layer. In contrast, for a joint reconstruction, the regularization is a joint regularization determined as a weighted combination of individual regularizations of the layers.

However, after a number of experiments, simulations, and testing, some embodiments identify additional problems of layered reconstruction. Indeed, why computational performance has been improved, the image quality of reconstructed images of the layers suffered. This quality degradation more noticeable on the images of the deeper layers. This problem is partially addressed by the joint reconstruction, but still, in a number of experiments, the images of the deeper layers reconstructed using individual and/or joint reconstruction include artifacts.

Some embodiments are based on recognition that despite the advantages of treating a target object as a layered-structure, such a treatment create an additional problem in the multi-level image reconstruction. Specifically, the multi-level image reconstruction suffers from shadow effect due to the non-uniform penetrating of the wave from front layer to deeper layers. This problem can be conceptualized as a structure of one layer casts a shadow on subsequent layers and that shadow can be considered as the structure of the subsequent layers. In such a manner, the shadow effect contributes to the artifacts in the image reconstruction of the deep layers.

FIG. 2 shows a schematic of the shadow effect of patterns from front layers to deep layers. The pattern 215 of a letter 'M' appears at the first layer 210 of the structure 130 and the pattern 225 of a letter 'E' appears at the second layer 220 of the structure 130. Due to the non-uniform penetration, a shadow letter of 'M' appears 240 on the second layer 220 and also appears 241 on a third layer 230. Likewise, a shadow letter of 'E' appears 250 on the third layer 230. It is an object of some embodiments to recover the patterns/letters 'M' and 'E' even in the presence of shadow effect.

Some embodiments are based on realization that the shadow effect prevents an increase in sparsity of the layers of the target object in the direction of propagation of the wave penetrating the layers of the object. Indeed, if each subsequent layer has a shadow effect from a previous layer, the subsequent layer is at least as sparse as the previous layer, but usually is less sparse. To that end, some embodiments are based on realization that if such a constraint is enforced on joint images reconstruction of the layers, such a constraint forces the reconstruction to consider shadow effect to reduce the unwanted artifacts.

Figure 3:
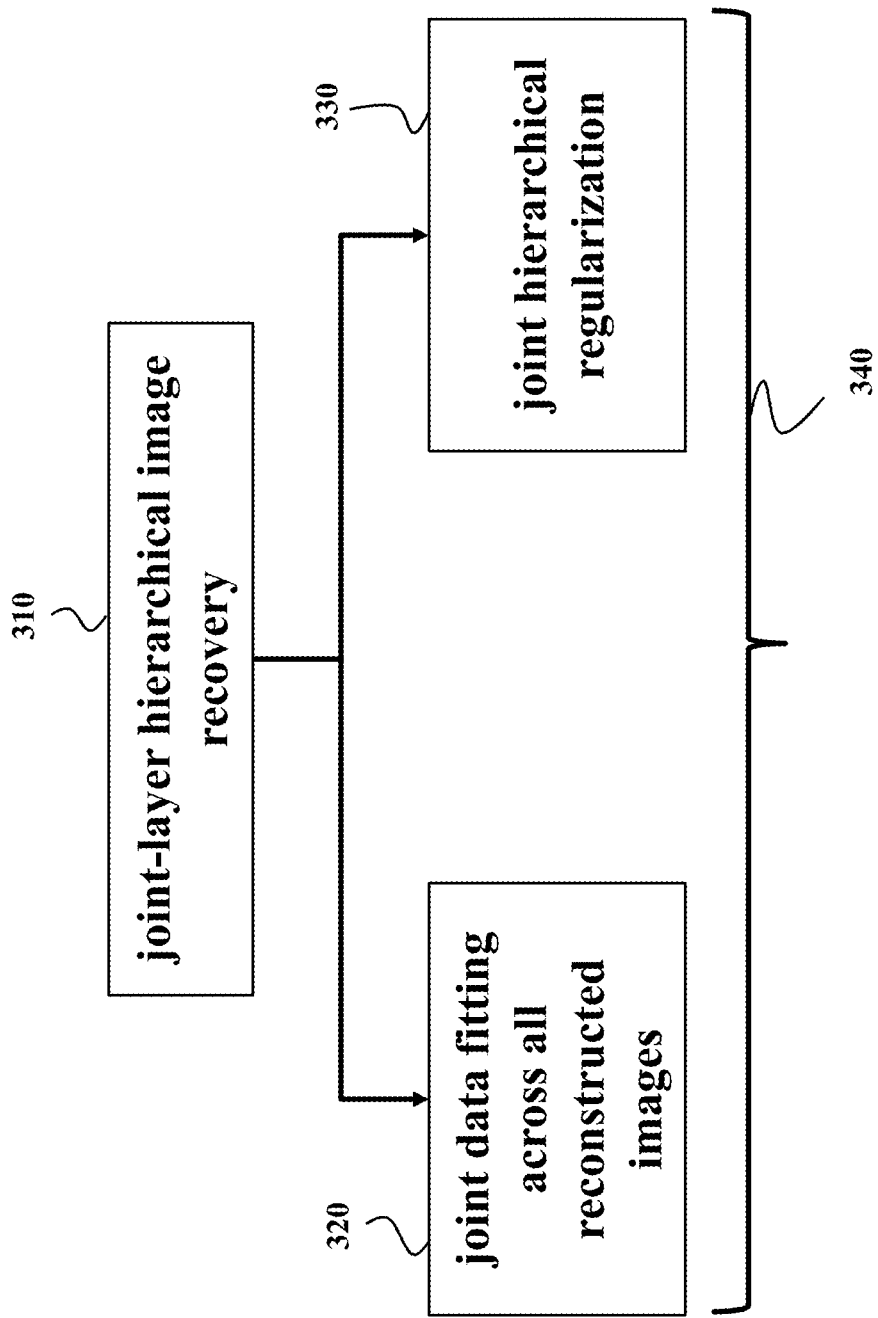
FIG. 3 shows a schematic of a joint-layer hierarchical image recovery according to some embodiments that prevents an increase in sparsity of the layers of the target object in the direction of propagation of the wave.

FIG. 3 shows a schematic of a joint-layer hierarchical image recovery 310 according to some embodiments that prevents an increase in sparsity of the layers of the target object in the direction of propagation of the wave. For example, the increase in sparsity of the layers can be prevented by imposing hierarchical joint sparsity constraints on image reconstruction.

For example, in one embodiment the joint-layer hierarchical image recovery uses a combination of a first term 320 and a second term 330. The first term 320 imposes a joint data fitting across all reconstructed images of all layers of the multi-layer structure to the measured intensities of the reflected wave. The second term 330 imposes the joint hierarchical regularization on recovered content of the reconstructed images of the multi-layer structure. For example, in one embodiment the joint-layer hierarchical image recovery 310 can use a regularized least square method minimizing 340 a combination of a first term and a second term. In such a manner, the joint-layer hierarchical image recovery can take advantage from joint image reconstruction while considering the shadow effect.

Figure 4:
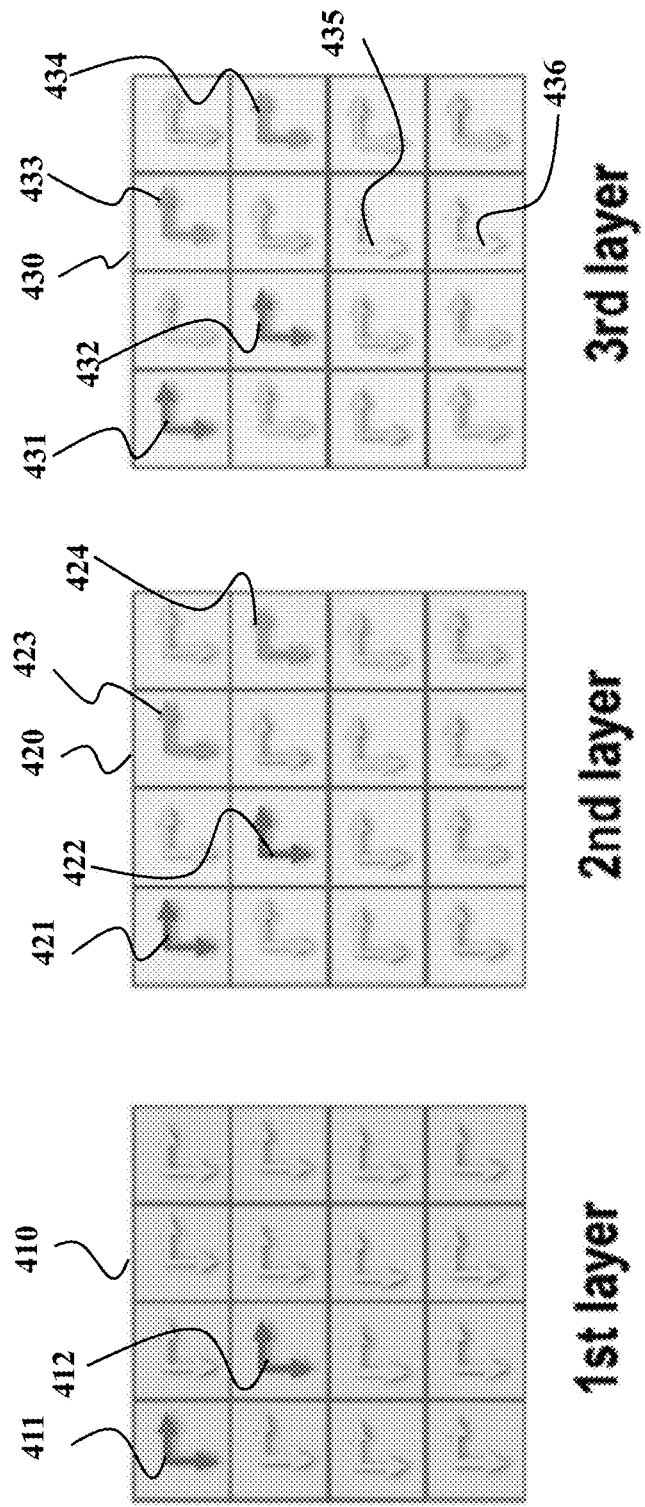
FIG. 4 shows a schematic illustrating the joint hierarchical regularization used by some embodiments.

FIG. 4 shows a schematic illustrating the joint hierarchical regularization used by some embodiments. The joint hierarchical regularization is illustrated using a schematic of three layers of paper of FIG. 2. FIG. 4 shows hierarchical group sparsity in the total variation (TV) domain advantageous for image reconstruction. The arrows 411-412 represent non-zero (horizontal/vertical) gradients of the first layer 410. The arrows 421-422 represent non-zero (horizontal/vertical) gradients of on the second layer 420 due to the shadow effect of the first layer 410. The arrows 423-424 represent non-zero (horizontal/vertical) gradients of the second layer 420. The arrows 431-432 represent non-zero (horizontal/vertical) gradients of on the third layer 430 due to the shadow effect of the first layer 410. The arrows 433-434 represent non-zero (horizontal/vertical) gradients of on the third layer 430 due to the shadow effect of the second layer 420. The arrows 435-436 represent non-zero (horizontal/vertical) gradients of the third layer 430. The rest of the arrows denote zero gradients.

The joint hierarchical regularization is a weighted combination of joint regularizations of group of layers, each group of layers includes a layer selected from the multi-layered structure as well as all layers preceding the layer in the multi-layer structure. In this context, a joint regularization of a group of layers is a weighted combination of individual regularizations of the layers in the group.

To that end, this example includes three group of layers. The first group includes only layer 410. The second group includes layers 410 and 420. The third group includes layers 410, 420, and 430. The joint regularization of a group of layers is a weighted combination of individual regularizations of the layers in the group. In different embodiments, individual regularizations are determined from the gradients of each layer independently of each other. Examples of regularizations include Tikhonov Norm-2 regularization, Norm-1 regularization and the like.

The weights for weighted combination of individual regularizations in determining a joint regularization and the weights for weighted combination of joint regularizations in determining the joint hierarchical regularization can be predetermined ad vary among different applications. The weights can be selected from prior knowledge on the hierarchical layered structures, or as equal values, or other means.

Figure 5:
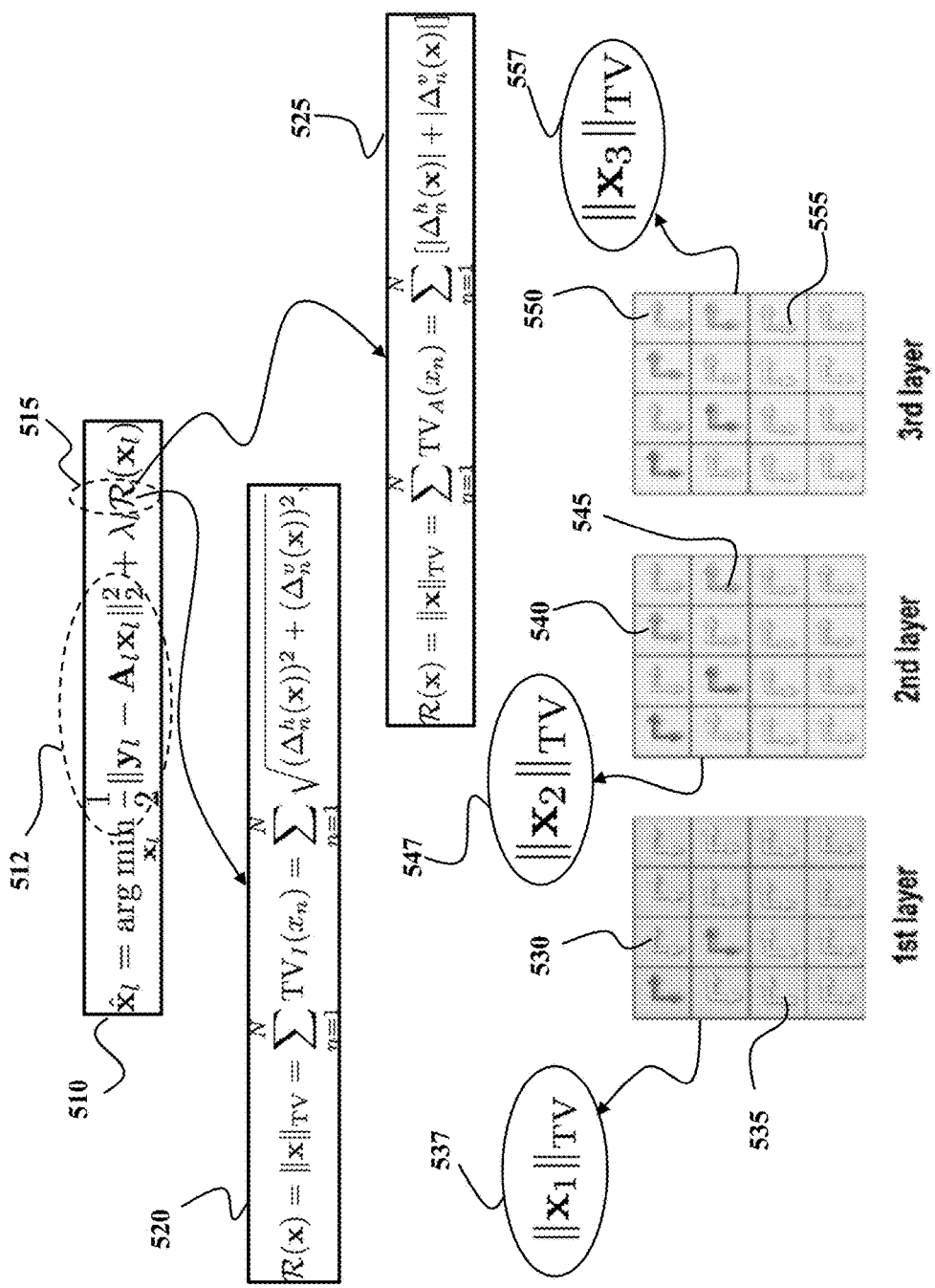
FIGS. 5, 6, and 7 show schematics of mathematical formulation of individual regularization, joint regularization, and joint hierarchical regularization according to some embodiments.
Figure 6:
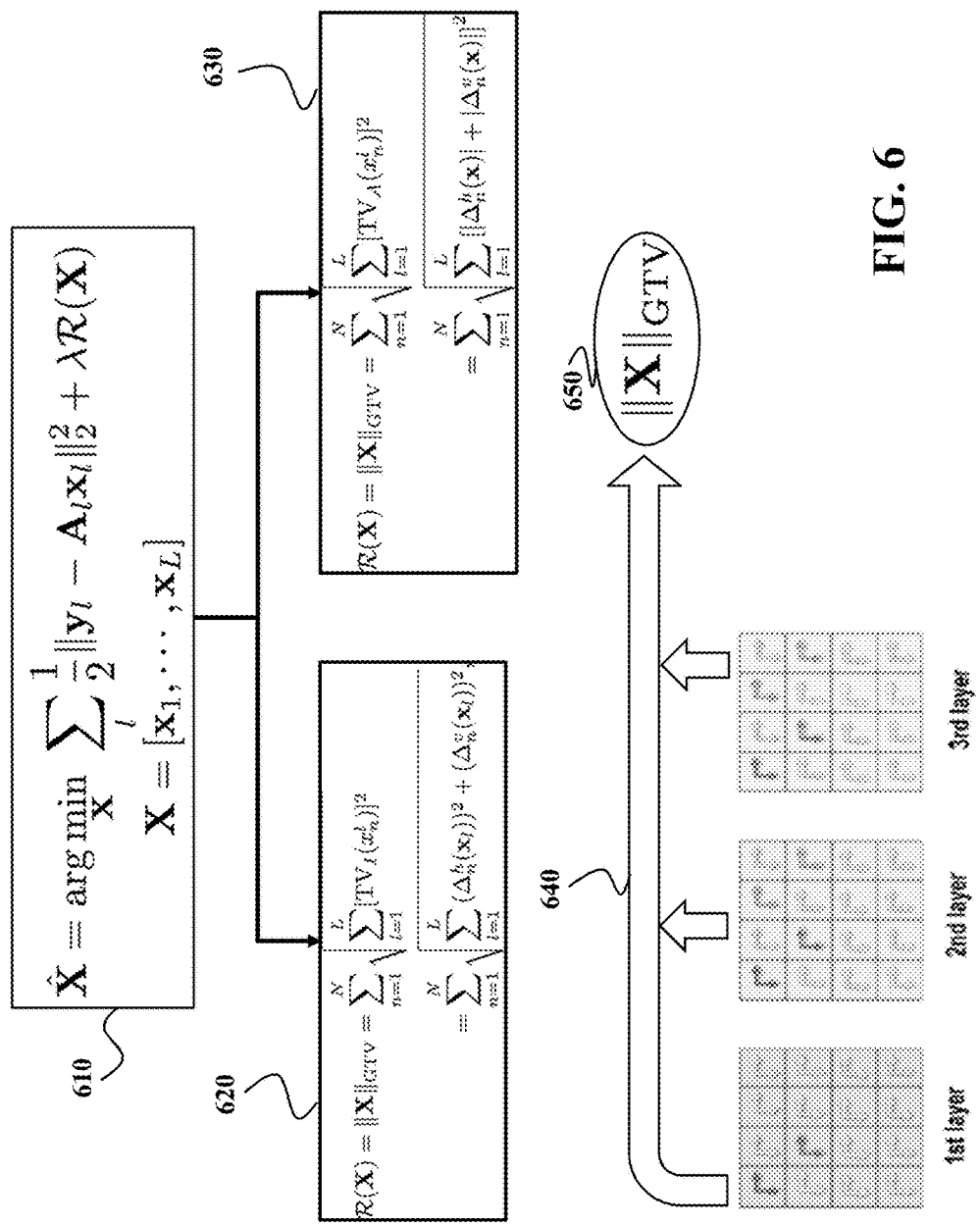
Figure 7:
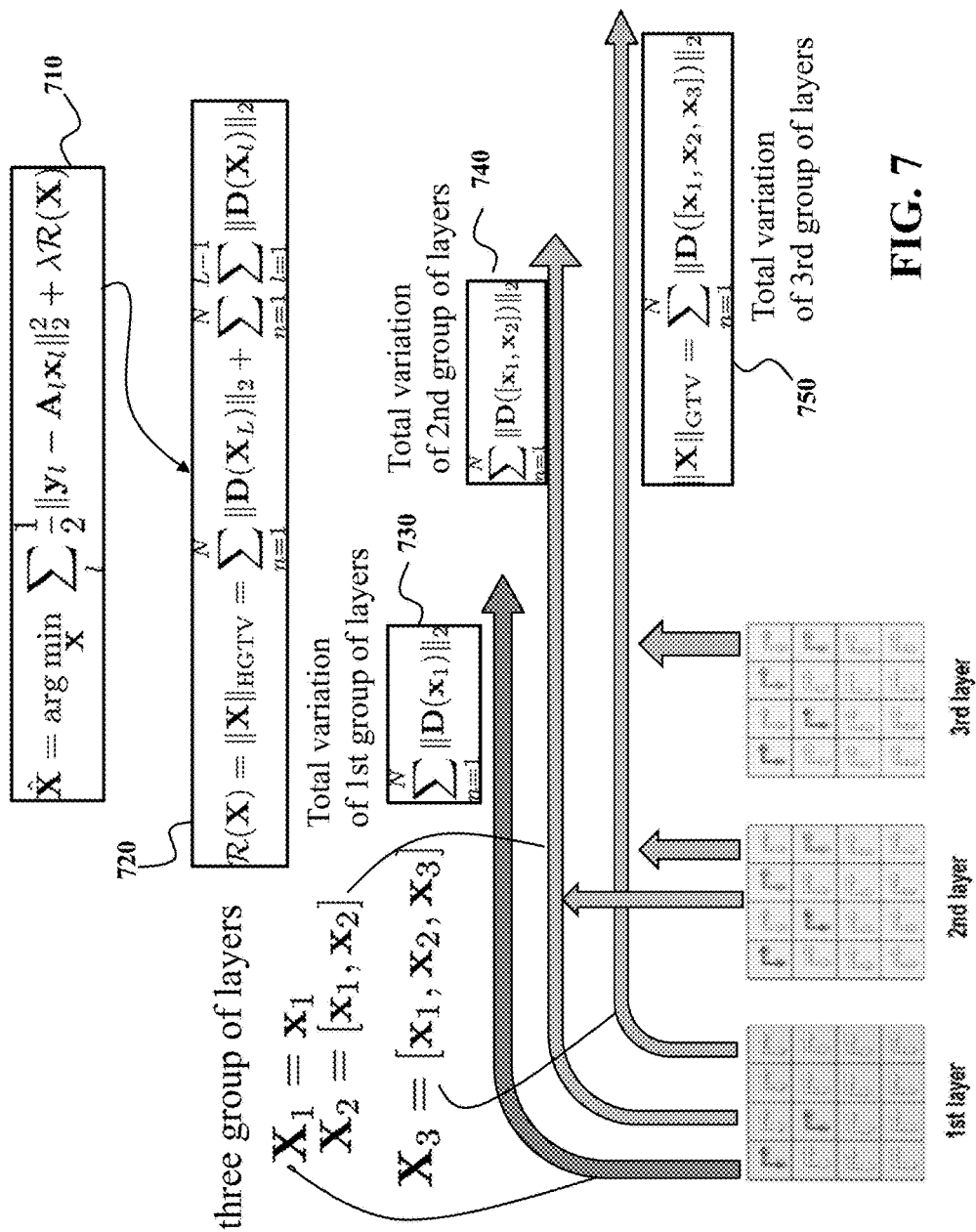

FIGS. 5, 6, and 7 show schematics of mathematical formulation of individual regularization, joint regularization, and joint hierarchical regularization according to some embodiments. Those examples use regularizations that includes TV of amplitudes of the measured intensities of the reflected wave. For example, the TV can be isotropic TV that computes the sum of the square root of the squared sum of horizontal and vertical gradients of individual pixels over all pixels each layer. For example, the TV can be anisotropic TV that computes the sum of the absolute value of horizontal and vertical gradients of individual pixels over all pixels each layer. In some implementations, the joint-layer hierarchical image recovery minimizes TV of amplitudes of the measured intensities of the reflected wave subject to hierarchical joint sparsity constraints.

FIG. 5 shows a schematic of individual-layer image recovery according to one embodiment. The individual-layer image recovery can be used to reconstruct images of multi-layered structure of the target object. For example, one implementation uses regularized least square solution 510. The regularized least square criterion includes two terms, one term 512 is for the data fitting and the other term imposing some form of individual regularization 515 on the recovered content on each layer. One choice of regularization is the total variation one which computes local gradients of each pixel. Two versions of total variation regularization can be used. One is the isotropic total variation 520 that is defined as the square root of the squared sum of horizontal and vertical gradients of individual layer. The other is the anisotropic total variation 525 that is defined as the sum of absolute values of horizontal and vertical gradients at individual layer.

FIG. 5 further shows an illustrative example of vertical and horizontal gradients (denoted as arrows) of an area of 4×4 pixels on layers 530, 540, and 550 of a three-layer structure. Some arrows represent zero gradients (no pixel-to-pixel amplitude changes) while others denote non-zero gradients (amplitude changes). Horizontal arrows, e.g., 530, 540, and 550, denote horizontal gradients. Vertical arrows, e.g., 535, 545, and 555, denote vertical gradients. The individual-layer regularization term is computed separately from the gradients from each layer. Examples of individual-layer regularization term include Tikhonov Norm-2 regularization, Norm-1 regularization, wavelet-domain regularization, and the like, 537, 547, and 557 computes the total variation at each individual layer of the three layers.

FIG. 6 shows a schematic of joint image recovery according to one embodiment. The joint-layer image recovery can be used to reconstruct images of multi-layered structure of the target object.

For example, one implementation uses joint-layer regularized least square solution 610. The joint-layer regularized least square criterion includes two terms, one for the total date fitting across all layers (L layers) and the other imposing some form of joint regularization on the recovered content on all layers. One choice of such regularization is the group total variation one that computes local gradients of each pixel of all layers. Two versions of group total variation regularization can be used. One is the isotropic group total variation 620 that is defined as the square root of the squared sum of horizontal and vertical gradients of all layers. The other is the anisotropic total variation 630 that is defined as the sum of absolute values of horizontal and vertical gradients of all layers. FIG. 6 further includes an illustrative example of vertical and horizontal gradients (denoted as arrows) of an area of 4×4 pixels on a three-layer structure. The joint-layer regularization term 650, such as the isotropic version 620 or the anisotropic version 630, is computed jointly 640 from the gradients at all three layers.

FIG. 7 shows a schematic of joint hierarchical image recovery according to one embodiment. The joint hierarchical image recovery can be used to reconstruct images of multi-layered structure of the target object. For example, one implementation uses a joint-layer hierarchical regularized least square solution 710. The joint-layer hierarchical regularized least square criterion includes two terms, one for the total data fitting across all layers (L layers) and the other imposing some form of joint hierarchical regularization on the recovered content on all layers. One choice of such regularization is the group hierarchical total variation 720 that computes local gradients of each pixel of all hierarchical groups of layers.

FIG. 7 further includes an illustrative example of vertical and horizontal gradients (denoted as arrows) of an area of 4×4 pixels on a three-layer structure. The joint hierarchical regularization term is computed from the gradients at all three layers in a hierarchical fashion. In such a manner, the regularization term 730 computes the total variation over the first group of layers (also the first layer), the regularization term 740 computes the total variation over the second group of layers (including the first and second layers), and the regularization term 750 computes the total variation over the third group of layer (including the first, second and third layers). Then the regularization term 720 sums over the total variations over all groups of layers, i.e., 730, 740 and 750 in this illustrative example. Such a nested calculation allows considering a shadow effect.

Figure 8:
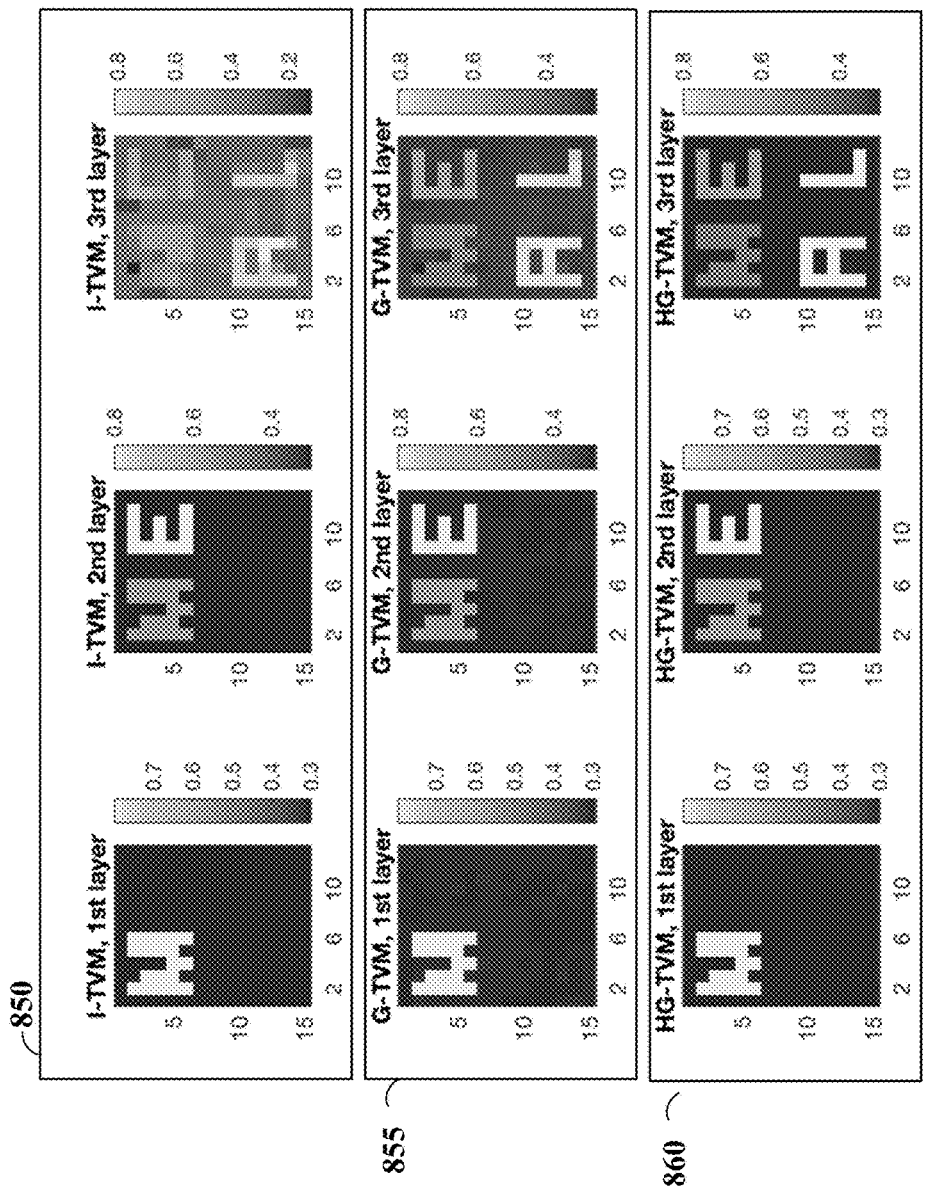
FIG. 8 shows an illustrative example of recovered multi-layer non-overlapping contents by one embodiment.

FIG. 8 shows an illustrative example of recovered multi-layer non-overlapping contents by one embodiment from a three-layer structure using the individual-layer 850, joint-layer 855, and joint-layer hierarchical 860 recovery. It is observed that the joint-layer hierarchical recovery gives the best result over three layers, especially for the third layer.

Figure 9:
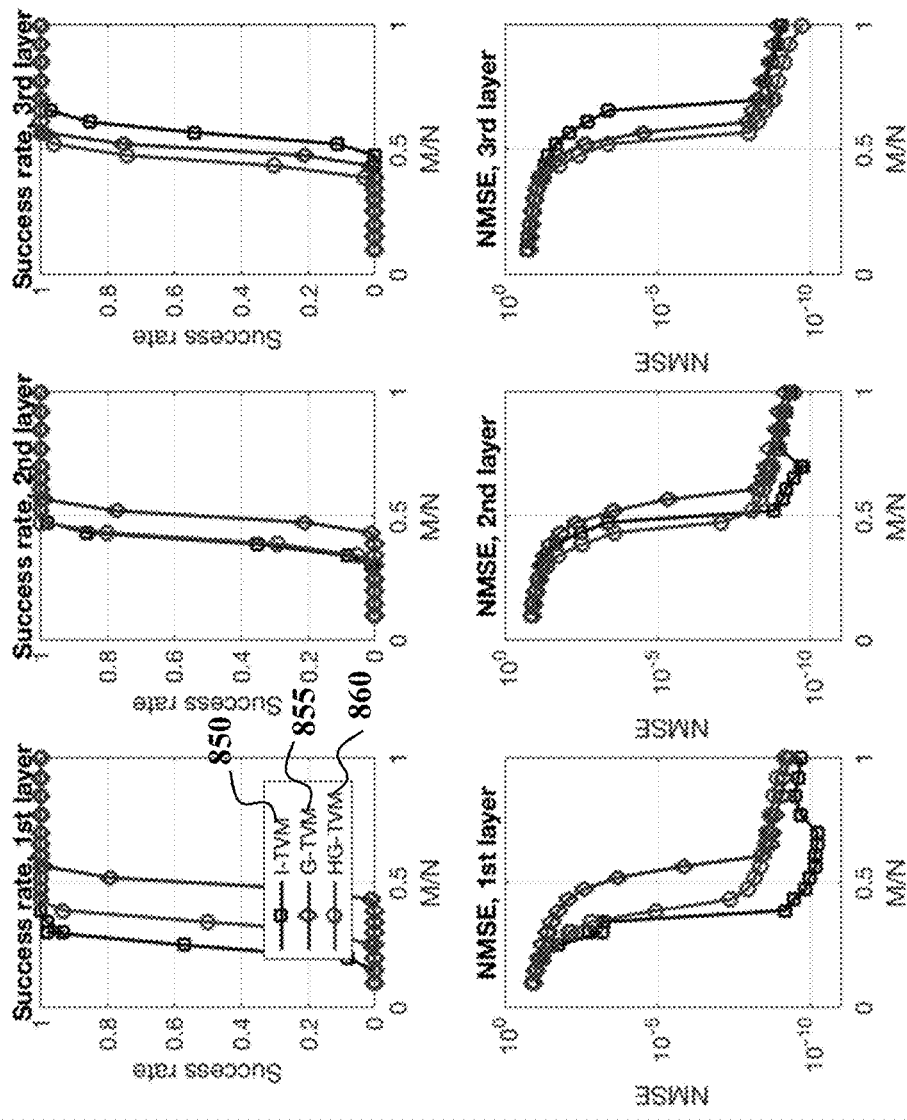
FIG. 9 shows statistics of recovered multi-layer non-overlapping contents according to different embodiments.

FIG. 9 shows statistics 910 of recovered multi-layer non-overlapping contents from a three-layer structure of FIG. 8 using the individual-layer 850 (denoted as squares), joint-layer 855 (denoted as diamonds), and joint-layer hierarchical 860 (denoted as circles) recovery in terms of success rate and normalized mean-squared error as a function of compression ratio.

Here, we provide more detailed descriptions of the individual-layer 850, joint-layer 855, and joint-layer hierarchical 860 recovery algorithms.

Individual-Layer TV Minimization 850

First, a straightforward solution is to apply the TV-regularized minimization independently over each individual layer. This solution can be formulated as follows $$\hat{x}_l = \underset{x_l}{\operatorname{argmin}} \frac{1}{2} \|y_l - A_l x_l\|_2^2 + \lambda_l \|x_l\|_{TV} \quad (2)$$

where $\lambda_l$ is the regularization parameter for the l-th layer, and $\text{PxP}_{TV}$ is a discrete TV (semi)-norm with two popular choices of 1) the isotropic TV $$\|x\|_{TV} = \sum_{n=1}^{N} TV_I(x_n) = \sum_{n=1}^{N} \sqrt{(\Delta_n^h(x))^2 + (\Delta_n^v(x))^2}, \quad (3)$$

and 2) the anisotropic TV $$\|x\|_{TV} = \sum_{n=1}^{N} TV_A(x_n) = \sum_{n=1}^{N} [|\Delta_n^h(x)| + |\Delta_n^v(x)|] \quad (4)$$

with the operators $\Delta_n^h(x)$ and $\Delta_n^v(x)$ correspond to, respectively, the horizontal and vertical first order differences at pixel n. Specifically, $\Delta_n^h(x) = x_n - x_{h(n)}$ and $\Delta_n^v(x) = x_n - x_{v(n)}$ with h(n) and v(n) denoting the nearest horizontal and vertical neighbors of pixel n, respectively. Fast algorithms such as iterative shrinkage/thresholding algorithms (ISTA) and its accelerated version (FISTA) have been proposed to circumvent the non-smoothness of the TV regularization term.

Joint-Layer TV Minimization 850

It is seen that the solutions from (2) do not explore the shadow effect and require more measurements for deep layers as the sparsity decreases over layers. To utilize the shadow effect, one can enforce the group sparsity over layers such that the content in front layers always appear in deep layers. One way to formulate this group sparsity over layers can be described as follows $$\hat{X} = \arg\min_X \sum_l \frac{1}{2} \|y_l - A_l x_l\|_2^2 + \lambda \|X\|_{GTV} \quad (5)$$

where $X = [x_1, \ldots, x_L] \in R^{N \times L}$ groups all images over L layers, $\lambda$ is the regularization parameter, $\|X\|_{GTV}$ is the group TV over multiple layers defined as $$\|X\|_{GTV} = \sum_{n=1}^{N} \sqrt{\sum_{l=1}^{L} [TV_I(x_n^l)]^2} \quad (6)$$

$$= \sum_{n=1}^{N} \sqrt{\sum_{l=1}^{L} (\Delta_n^h(x_l))^2 + (\Delta_n^v(x_l))^2},$$

for the isotropic TV and $$\|X\|_{GTV} = \sum_{n=1}^{N} \sqrt{\sum_{l=1}^{L} [TV_A(x_n^l)]^2} \quad (7)$$

$$= \sum_{n=1}^{N} \sqrt{\sum_{l=1}^{L} [|\Delta_n^h(x)| + |\Delta_n^v(x)|]^2},$$

for the anisotropic TV. It is noted that, for a given pixel n, instead of 2 (horizontal and vertical) gradients in the single-layer case, there are 2L gradients over L layers. The isotropic group TV simply uses the $\ell_2$ norm over the expanded 2L gradients followed by the $\ell_1$ norm over all pixels.

Hierarchical Joint-Layer TV Minimization

In addition to the shadow effect, the non-overlapping assumption imposes an additional feature over layers, i.e., the TV-domain sparsity extent increases over layers, i.e., $S(TV(x_l)) \subset S(TV(x_{l+1}))$, where $S(x)$ is the set of indices where the elements of x are non-zeros. In fact, the combined shadow effect and non-overlapping assumption introduces a hierarchical layer-wise structure in the TV domain.

As an illustrative example of L=3 in FIG. 4 where non-zero and zero gradient denoted as color and gray arrows, respectively, two pixels with non-zero (horizontal and vertical) gradients are present in the upper left corner of the first layer and, due to the shadow effect, the gradients of the same pixels at the second and third layers are also non-zeros. At the second layer, two more pixels at the upper right corner have non-zero gradients which results in the same pixels at the third layer have non-zero gradients. Finally, at the third layer, two more pixels at the lower right corner have non-zero gradients. From this illustrative example, one can clearly see that the hierarchical structure over layers. To be more precise, it is a nested group sparsity pattern over layers in the TV domain.

The nested group structure can be mathematically formulated as follows. Denote the l-th layer image as $X_l \in R^{N_r \times N_c}$ where $N = N_r \times N_c$, where $x_l$ is the vectorized version of $X_l$. We can define the matrix $I_{TV}$ below indicating the smallest layer index where a pixel has non-zero gradients $$[I_{TV}]_{n_r,n_c} = \begin{cases} \min_l \{TV([X_l]_{n_r,n_c}) \neq 0\} \\ 0, \text{ if } TV([X_l]_{n_r,n_c}) = 0, l = 1, \ldots, L \end{cases} \quad (9)$$

For the illustrative example in FIG. 4, the corresponding matrix $I_{TV}$ is given at the right upper corner. For a given pixel at $[n_r, n_c]$, the nested group structure implies that $$TV([X_l]_{n_r,n_c}) = 0, \text{ for all } l < [I_{TV}]_{n_r,n_c}. \quad (10)$$

In other words, all gradients at layers before the layer $[I_{TV}]_{n_r,n_c}$ are all zeros. On the other hand, the number of non-zero gradients for the pixel at $[n_r, n_c]$ over layers is equal to the number of layers minus the corresponding smallest layer index in $I_{TV}$.

$$[H_{TV}]_{n_r,n_c} = L - [I_{TV}]_{n_r,n_c}, \text{ if } [I_{TV}]_{n_r,n_c} > 0. \quad (11)$$

For the problem of interest here, we introduce hierarchical sparsity constraints to the TV domain. To describe the hierarchical group structure, we define the following variables $$X_l = [x_1, \ldots, x_l] \in R^{N \times l} \quad (12)$$

$$D(X_l) = [d_1, d_2, \ldots, d_l] \in R^{N \times l} \quad (13)$$

where $d_l = TV(x_l) = [TV(x_l(1)), \ldots, TV(x_l(N))]^T$ denotes the (isotropic or anisotropic) TV vector of $x_l$ at the l-th layer. Essentially, $D(X_l)$ groups the first l TV vectors for the first l layers. Note that $D_1 = d_1$. Then the hierarchical group TV minimization over multiple layers is defined as follows $$\hat{X} = \arg\min_X \sum_l \frac{1}{2} \|y_l - A_l X_l\|_2^2 + \lambda \|X\|_{HGTV} \quad (14)$$

where $$\|X\|_{HGTV} = \sum_{n=1}^{N} \sum_{l=1}^{L} \|D(X_l)\|_2 \quad (15)$$

with each $\|D(X_l)\|_2$ imposed for attaining the group structure from the first layer to the l-th layer. We can rewrite $$\|X\|_{HGTV} = \sum_{n=1}^{N} \|D(X_L)\|_2 + \sum_{n=1}^{N} \sum_{l=1}^{L-1} \|D(X_l)\|_2 \quad (16)$$

Then additional penalty terms $\sum_{n=1}^{N}\sum_{i=1}^{L-1}\|D(X_l)\|_2$ enforce extra sparsity constraints when the layer index l becomes smaller. As a result, it encourages more sparse solutions at the front layers than the deep layers and, therefore, gives a solution with the nested group sparse pattern in the TV domain.

Figure 10:
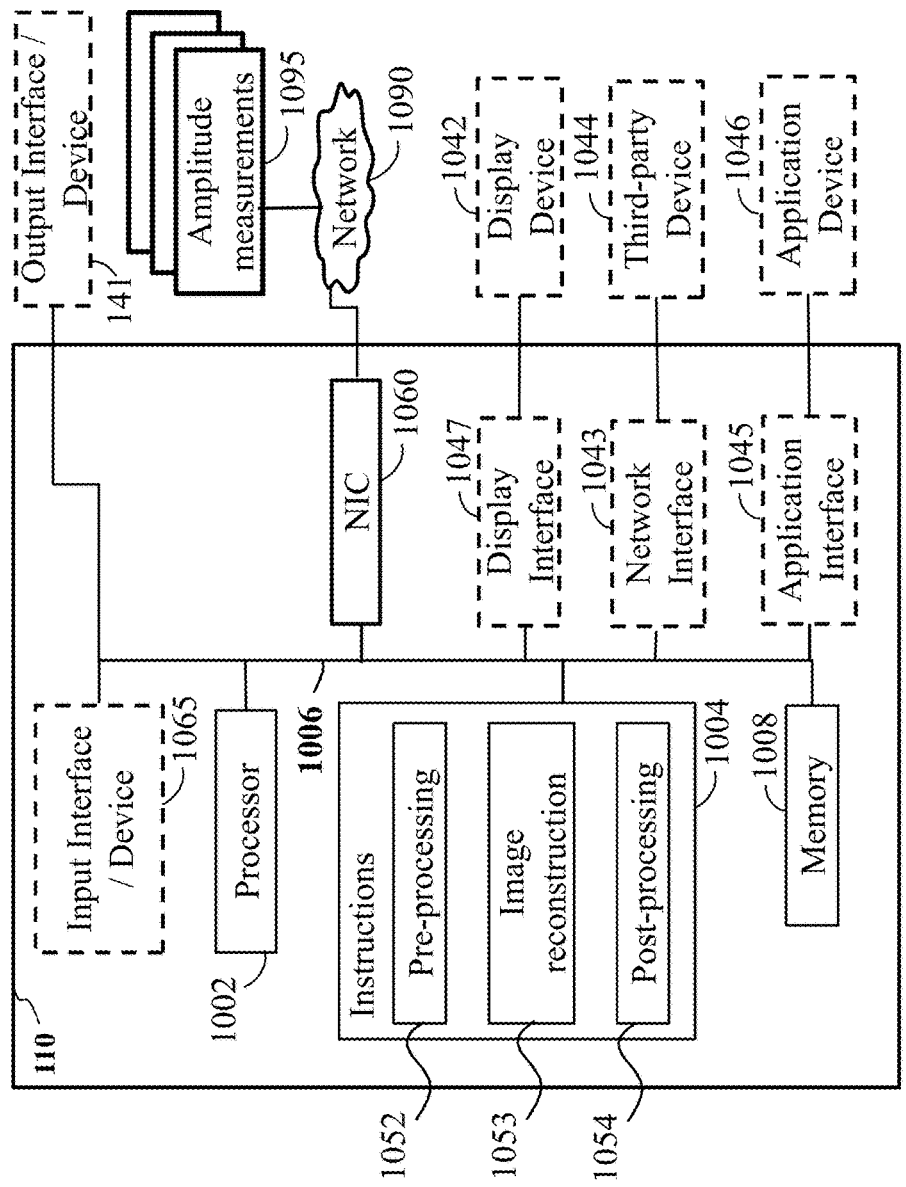
FIG. 10 shows a block diagram of a computer-based information system in accordance with some embodiments.

FIG. 10 shows a block diagram of a computer-based information system 110 in accordance with some embodiments. The information system 110 can include a processor 1002 configured to execute stored instructions, as well as a memory 1008 that can store instructions executable by the processor. The processor 1002 can be a single core processor, a multi-core processor, a computing cluster, or any number of other configurations. The memory 1008 can include random access memory (RAM), read only memory (ROM), flash memory, or any other suitable non-transitory computer readable storage medium. The processor 1002 is connected through a bus 1006 to one or more input interface/device 1065 and output interface/device 141.

These instructions 1004 stored in the memory 1008 can implement image recovery of a structure of the target object. For example, the instructions can include a pre-processing 1052, such as filtering, partitioning, time-gating, peak finding, and denoising on the measurements 1095 of the reflected wave. The instructions further provide the implementations of the image reconstruction 1053 according to different embodiments. Optionally, the instructions can include post-processing to further improve the quality of the reconstructed images and/or to combine the reconstructed images of the layers of the target object to produce an image of the structure of the target object.

The information system 110 can include an output interface/device 141 to render the estimated information. In some embodiments, the output interface 141 may include a printer interface (not shown) adapted to connect the encoder to a printing device (not shown). In some embodiments, a display interface 1047 can be adapted to connect the processor 102 to a display device 1042. The display device 1042 can include a camera, computer, scanner, mobile device, webcam, or any combination thereof. In some embodiments, a network interface 1043 is adapted to connect the processor 102 and also potentially to one or several third party devices 1044 on the network 1090. In some embodiments, an application interface 1045 can be used to submit the estimated information to an application device 1046, such as a controller, by non-limiting example, controlling the motion of the mobile object.

The information system 110 can also include an input interface 1065 to receive the amplitude measurements 1095 of the amplitude of the reflected signal 129. For example, a network interface controller (NIC) 1060 can be adapted to connect the information system 110 through the bus 1006 to the network 1090. The network 1090 can be implemented as the wired or wireless network. Through the network 1090 and/or other implementations of the input interface 1065, the measurements 1095 of the amplitude of the reflected signal can be downloaded and stored for storage and/or further processing.

Figure 11:
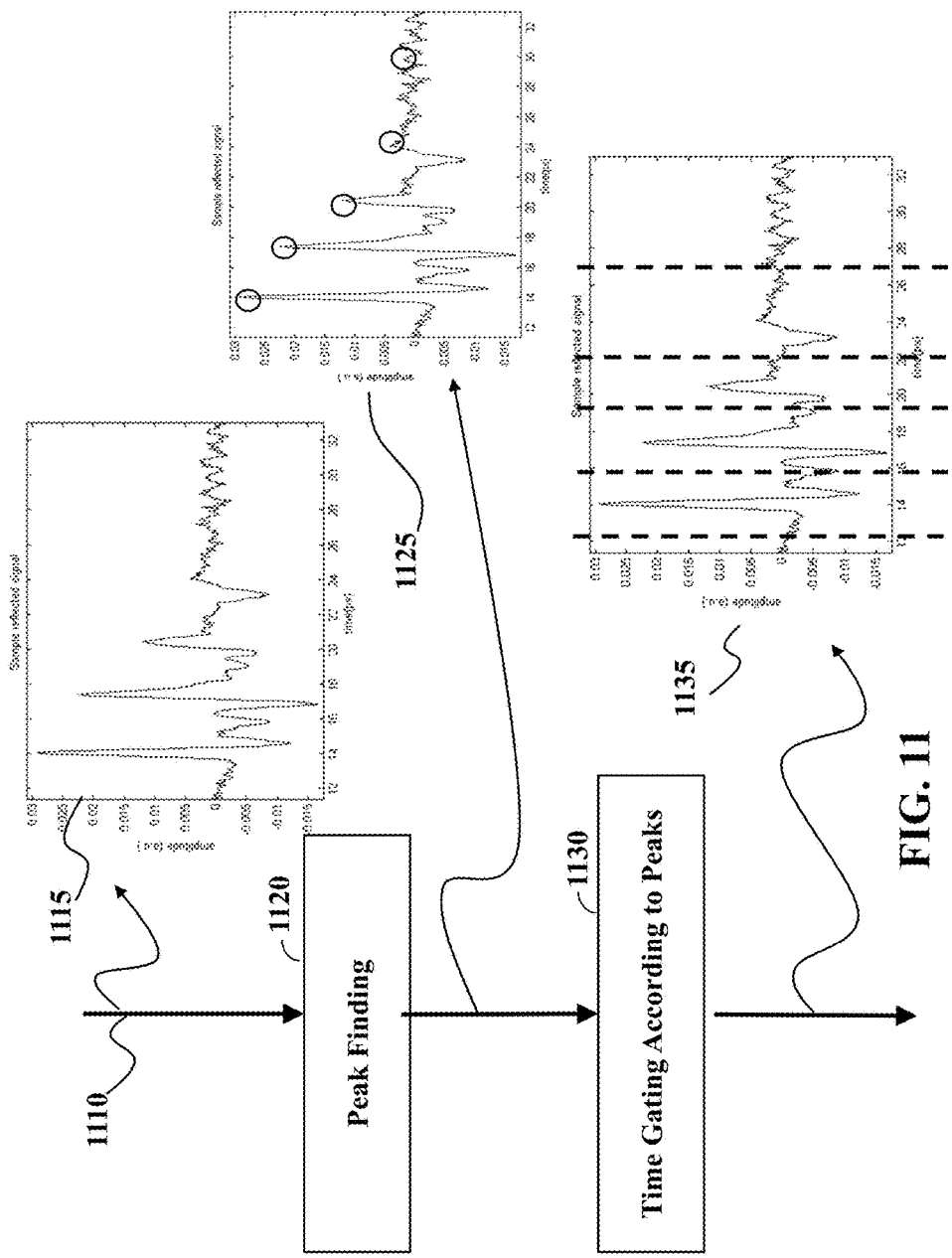
FIG. 11 shows a schematic of partitioning the reflected wave into a set of segments according to some embodiments.

FIG. 11 shows a schematic of partitioning the reflected wave into a set of segments according to some embodiments. The reflected wave 1115 from a target object is fed into a peak finding method 1120 to identify the peaks 1125 of the reflected wave. The time gating 1130 partitions the reflected wave 1115 around the peaks to produce the segments 1124. For example, one embodiment partitions the signal at a center point between two neighboring peaks. Additionally, or alternatively, one embodiment partitions the reflected wave at an equal segment to avoid peak finding process.

Different embodiments use different types of emitters selected based on an expected structure of the target object and desired type of image reconstruction. Examples of emitters include optical, ultrasound, and x-ray emitters. Some embodiments use terahertz (THz) emitters emitting within a terahertz frequency range, e.g., from 0.3 to 3 terahertz with corresponding wavelengths from 1 mm to 0.1 mm (or 100 µm). Because THz scanners are sensitive to non-uniform penetrating illumination from front layers to deep layers, the joint-layer hierarchical image recovery benefits these kinds of emitters.

Figure 12A:
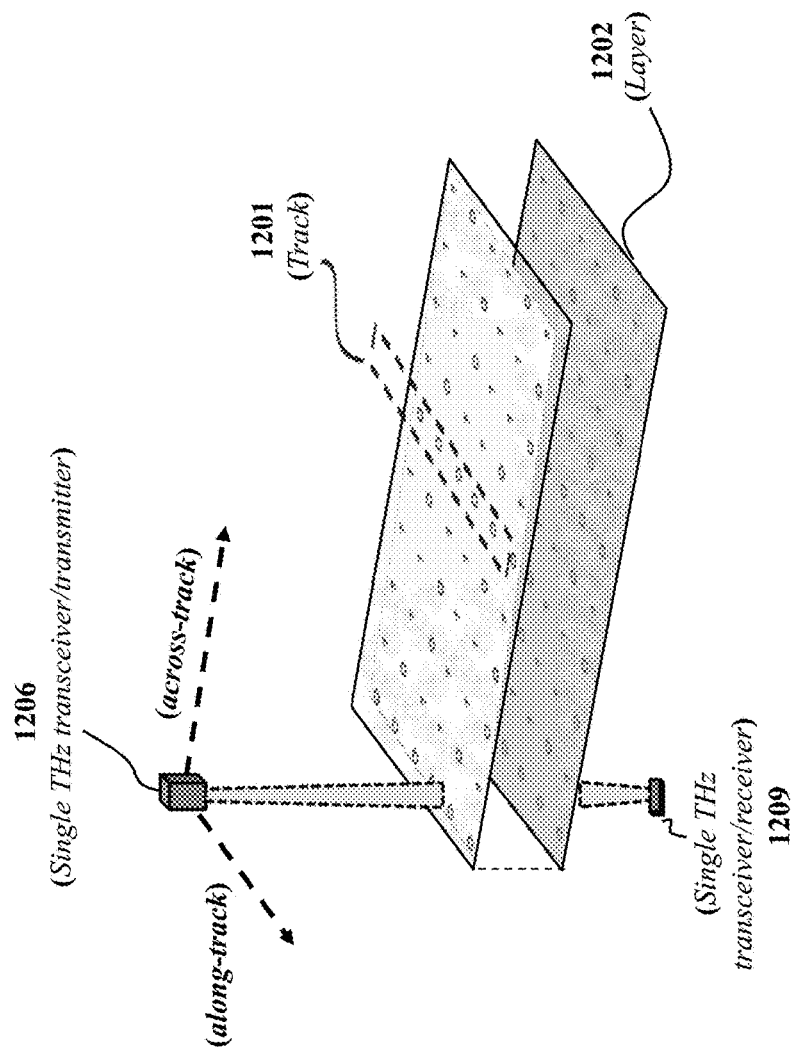
FIGS. 12A, 12B, 12C, and 12D show a schematic of THz scanners according to different embodiments.

FIG. 12A shows a schematic of using a single THz transceiver 1206 to mechanically scan the multi-layer 1202, multi-track 1201, multi-level scale, i.e., across the track and along the track, to receive the reflected waveforms to identify the coded pattern for the position. Alternatively, the single THz transceiver can be a transmitter, wherein the transmitted THz waveform passes through the multi-layered scale, and is received by a receiver 1209. In particular, the transmitted THz waveform passes through the multi-layered/multi-level scale, and the THz waveform continues directly to the receiver 1209 to identify the coded pattern for the position.

Figure 12B:
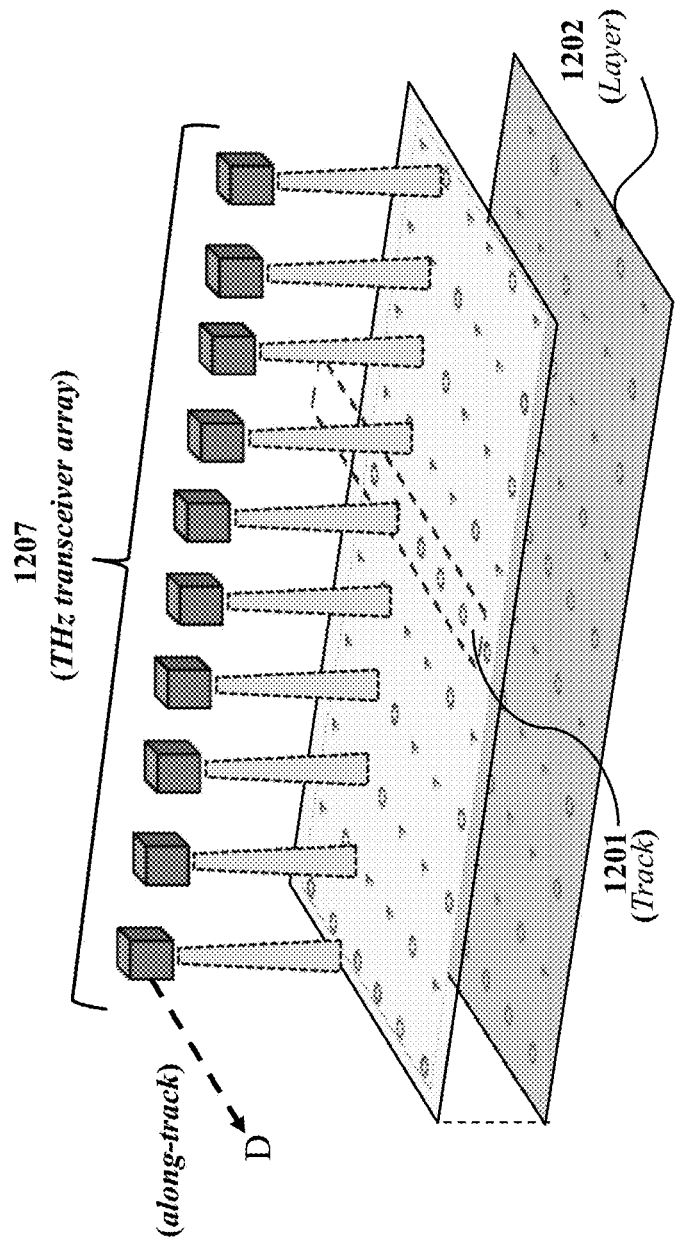

FIG. 12B shows a schematic of using multiple THz transceivers 1207 (or a THz transceiver array), wherein each THz transceiver in the array can be aligned with a single track 1201. Each THz transceiver can also be able to receive the reflected waveforms to identify the coded pattern of corresponding track for the position. The THz transceiver array 1207 can move simultaneously along the track direction D for absolute positioning.

Figure 12C:
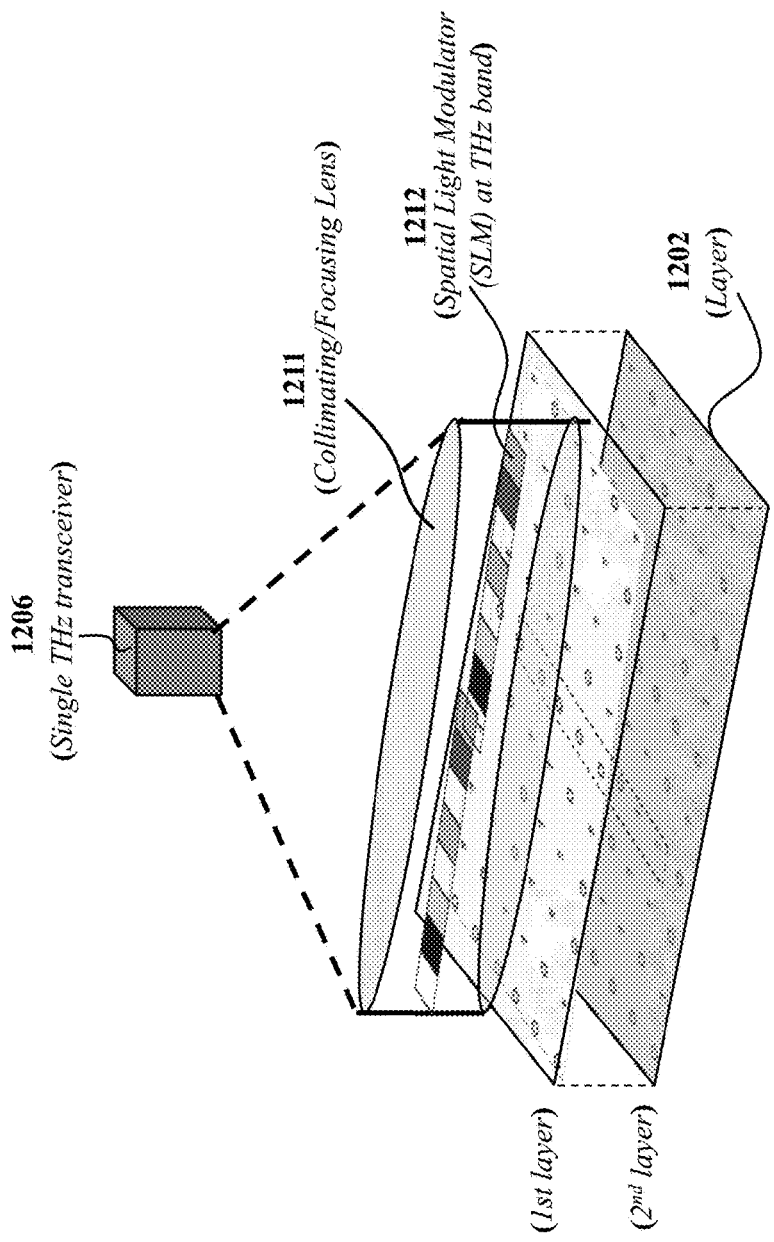

FIG. 12C shows a schematic of using a single THz transceiver 1206 together with collimating/focusing lenses 1211, spatial light modulators 1212 at the THz band. The single transceiver 1206 sends the THz waveform to the collimating lens 1211. The waveform is collimated by the collimating lens 1211 and then modulated by the spatial light modulator 1212 with random patterns. The reflected THz waveform passes through the focusing lens 1211 and detected by the single THz transceiver 1206.

Figure 12D:
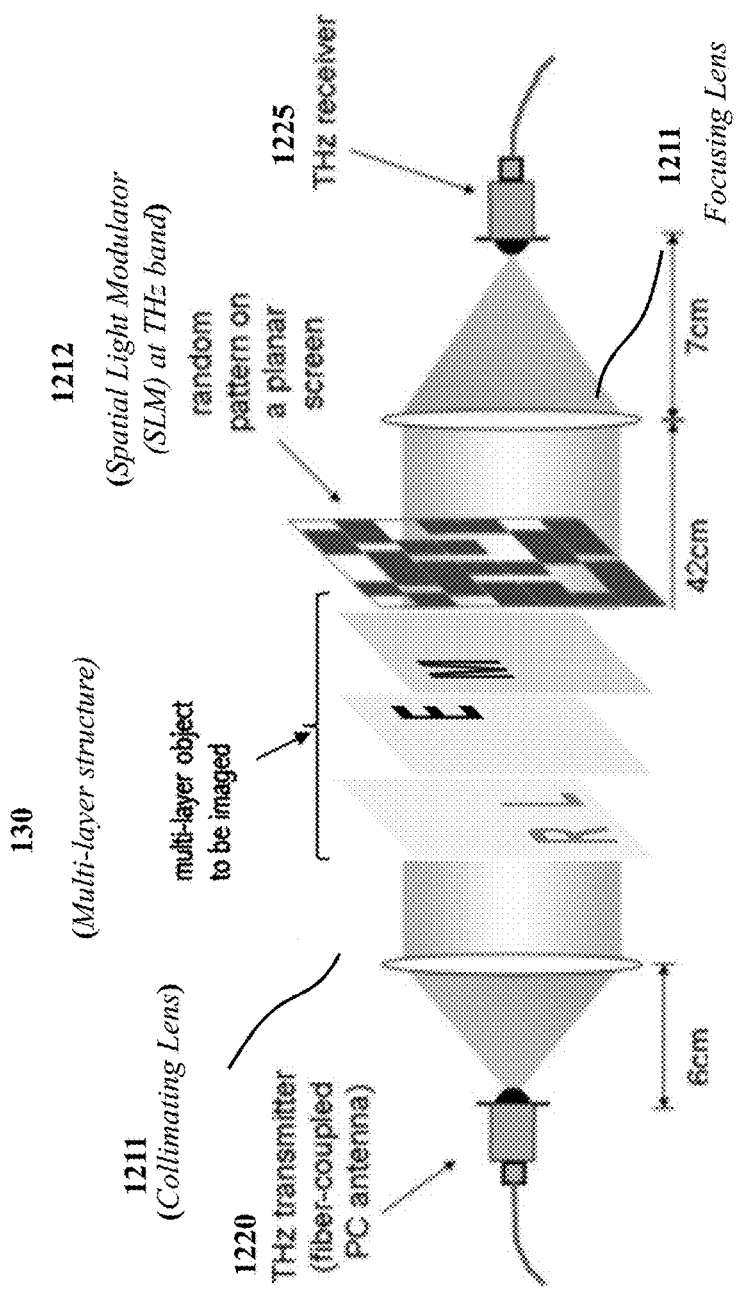

FIG. 12D shows a schematic of using a THz transmitter 1220 and a THz receiver 1225 separated on both sides of a multi-layer non-overlapping sample 130, along with collimating/focusing lenses 1211, spatial light modulators 1212 at the THz band. This acquisition is similar to FIG. 12C but in a transmission mode.

Some embodiments are based on another realization that the performance of joint-layer hierarchical image recovery can be improved when structural patterns of different layers of the target object are not overlapping in the direction of propagation of the wave. In such a manner, the shadow effect does not interfere with the structure of the subsequent layers. Some embodiments are based on recognition that in a number of situation, the structure of the target object is sparse enough to assume the non-overlapping patterns of different layers. Additionally, or alternatively, some embodiments design the target object in such a way as to ensure the non-overlapping patterns.

For example, in one embodiment the target object is a shipping label having an address printed on a first layer, and having a name of addressing printed on a second layer. The name and the address printed on different layers of the shipping label are not overlapping, and the name printed at the subsequent layer allows to preserve the confidentiality of the addressee. In another embodiment, the target object is an identification card having different identification codes printed on different layers of the identification card. Such an identification card allows to address a counterfeiting problem. In another embodiment, the target object is a position encoding structure having different codes printed on different layers of the position encoding structure. This embodiment allows to print a more dense code on multiple layers than a code printed only at a single layer.

Figure 13:
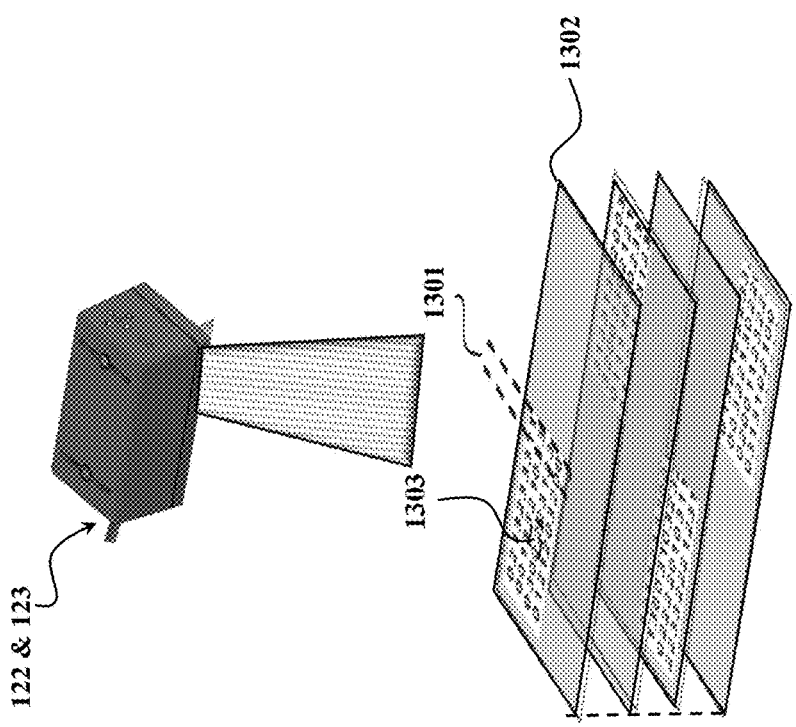
FIG. 13 shows a schematic illustrating a multi-layer structure with non-overlapping patterns over layers, according to one embodiment.

FIG. 13 is a schematic illustrating a multi-layer structure with non-overlapping patterns over layers, according to one embodiment. The layered structure includes multiple tracks 401 of coded patterns and multiple layers 402 of coded patterns. In each track, the number 403 specifies a level of reflectance of the coded pattern in the THz band. For example, 0 means a complete absorption of THz emitted signal, while 1 means a strong reflection of THz emitted signal. The number 403 can be binary or multi-level with a pre-defined mapping between the reflectance and the number. THz scanning over multi-layer non-overlapping patterns of this embodiment can be used for positioning in elevator/train systems.

Figure 14:
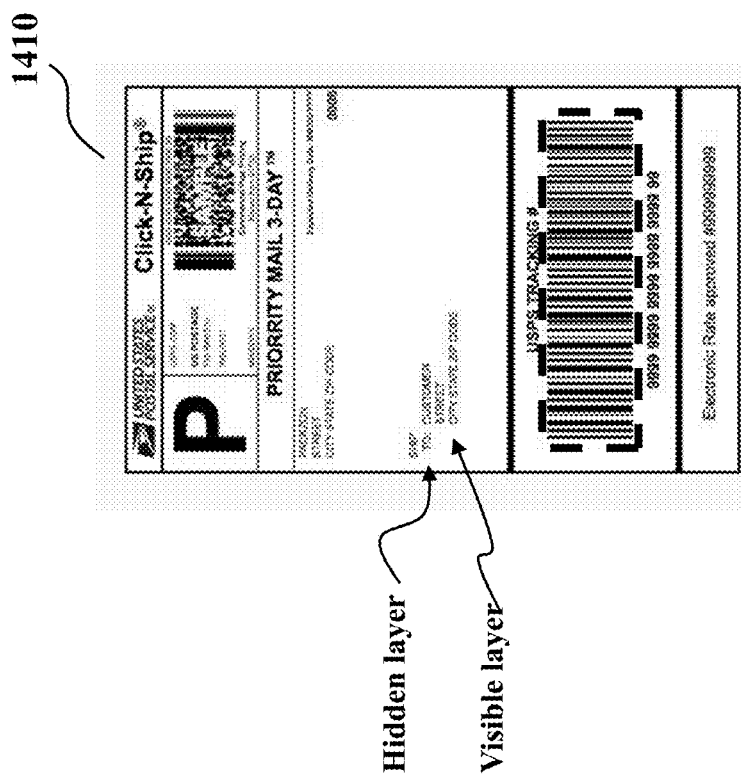
FIG. 14 shows a schematic of a shipping label with multi-layer non-overlapping contents, according to some embodiments.

FIG. 14 shows a schematic of a shipping label 1410 with multi-layer non-overlapping contents, according to some embodiments of the present disclosure. The multi-layer non-overlapping content can be used to preserve privacy-related contents in the deeper layers without visually disclosure on the surface. For example, the name and the address printed on different layers of the shipping label are not overlapping, and the name printed at the subsequent layer allows to preserve the confidentiality of the addressee.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers. Such processors may be implemented as integrated circuits, with one or more processors in an integrated circuit component. Though, a processor may be implemented using circuitry in any suitable format.

Also, the embodiments of the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Although the invention has been described by way of examples of preferred embodiments, it is to be understood that various other adaptations and modifications can be made within the spirit and scope of the invention.

Therefore, it is the object of the appended claims to cover all such variations and modifications as come within the true spirit and scope of the invention.

We claim:

1. A scanner, comprising:
   an emitter configured to emit a wave in a direction of propagation to penetrate layers of a structure of a target object;
   a receiver configured to measure intensities of the wave reflected by the layers of the target object;
   a hardware processor configured to
      partition the intensities of the reflected wave into a set of segments, such that each segment is the reflection from a corresponding layer of the target object, defining a multi-layered structure of the target object; and
      reconstruct images of the layers of the target object from corresponding segments using a joint-layer hierarchical image recovery that prevents an increase in sparsity of the layers of the target object in the direction of propagation of the wave; and
   an output interface to render the reconstructed images of layers of the target object.

2. The scanner of claim 1, wherein the joint-layer hierarchical image recovery reconstructs the images using a joint hierarchical regularization, wherein the joint hierarchical regularization is a weighted combination of joint regularizations of groups of layers, each group of layers includes a layer selected from the multi-layered structure as well as all layers preceding the layer in the multi-layer structure, and wherein a joint regularization of a group of layers is a weighted combination of individual regularizations of the layers in the group.

3. The scanner of claim 2, wherein the joint-layer hierarchical image recovery uses a joint-layer hierarchical regularized least square method minimizing a combination of a first term and a second term, wherein the first term imposes a joint data fitting across all reconstructed images of all layers of the multi-layer structure to the measured intensities of the reflected wave, and wherein the second term imposes the joint hierarchical regularization on recovered content of the reconstructed images of the multi-layer structure.

4. The scanner of claim 2, wherein the joint hierarchical regularization includes a total variation (TV) of amplitudes of the measured intensities of the reflected wave.

5. The scanner of claim 4, wherein the TV is one or combination of an isotropic TV and anisotropic TV.

6. The scanner of claim 1, wherein the joint-layer hierarchical image recovery minimizes a total variation (TV) of amplitudes of the measured intensities of the reflected wave subject to hierarchical joint sparsity constraints.

7. The scanner of claim 1, wherein the processor is configured to
   combine the reconstructed images of the layers of the target object to produce an image of the structure of the target object.

8. The scanner of claim 1, wherein the processor is configured to post-process at least some layers based on the images of the previous layers.

9. The scanner of claim 1, wherein the processor partitions the reflected wave using one or combination of a time-gating and a peak finding.

10. The scanner of claim 1, further comprising:
a memory configured to store data indicative of material of the layers of the target object, wherein the processor partitions the reflected wave based on the data.

11. The scanner of claim 1, wherein the emitter emits the wave within a terahertz frequency range.

12. The scanner of claim 11, wherein the terahertz frequency range is from 0.3 to 3 terahertz.

13. The scanner of claim 1, wherein the scanner operates in a compressed scanning mode,
wherein the emitter includes a collimator to collimate the wave to a broad beam, and a spatial encoder to spatially encode the broad beam with a random mask;
wherein the receiver includes a focusing lens to focus the reflected wave, and a single-pixel photoconductive detector receiving the focused wave from the focusing lens to provide one measurement of the focused wave at a time; and
wherein the hardware processor recovers the image of the multi-layer structure using a sparse reconstruction.

14. The scanner of claim 1, wherein structural patterns of different layers of the target object are not overlapping in the direction of propagation of the wave.

15. The scanner of claim 14, wherein the target object is a shipping label having an address printed on a first layer, and having a name of addressing printed on a second layer.

16. The scanner of claim 14, wherein the target object is an identification card having different identification codes printed on different layers of the identification card.

17. The scanner of claim 14, wherein the target object is a position encoding structure having different codes printed on different layers of the position encoding structure.

18. A method for image reconstruction of a structure of a target object, wherein the method uses a processor coupled with stored instructions implementing the method, wherein the instructions, when executed by the processor carry out steps of the method, comprising:
accepting intensities of the reflected wave, in response to emitting a wave in a direction of propagation to penetrate layers of a structure of a target object and measuring the intensities of the wave reflected by the layers of the target object;
partitioning the intensities of the reflected wave into a set of segments, such that each segment is the reflection from a corresponding layer of the target object, defining a multi-layered structure of the target object;
reconstructing images of the layers of the target object from corresponding segments using a joint-layer hierarchical image recovery that prevents an increase in sparsity of the layers of the target object in the direction of propagation of the wave; and
rendering the reconstructed images of layers of the target object.

19. The method of claim 18, wherein the joint-layer hierarchical image recovery reconstructs the images using a joint hierarchical regularization, wherein the joint hierarchical regularization is a weighted combination of joint regularizations of group of layers, each group of layers includes a layer selected from the multi-layered structure as well as all layers preceding the layer in the multi-layer structure, and wherein a joint regularization of a group of layers is a weighted combination of individual regularizations of the layers in the group.

20. A non-transitory computer readable storage medium embodied thereon a program executable by a processor for performing a method, the method comprising:
accepting intensities of the reflected wave, in response to emitting a wave in a direction of propagation to penetrate layers of a structure of a target object and measuring the intensities of the wave reflected by the layers of the target object;
partitioning the intensities of the reflected wave into a set of segments, such that each segment is the reflection from a corresponding layer of the target object, defining a multi-layered structure of the target object;
reconstructing images of the layers of the target object from corresponding segments using a joint-layer hierarchical image recovery that prevents an increase in sparsity of the layers of the target object in the direction of propagation of the wave; and
rendering the reconstructed images of layers of the target object.

* * * * *